(12) United States Patent
Abt et al.

(10) Patent No.: US 11,490,915 B2
(45) Date of Patent: Nov. 8, 2022

(54) ACTUATION MECHANISM WITH GROOVED ACTUATION LEVERS

(71) Applicant: Alcon Inc., Fribourg (CH)

(72) Inventors: Niels Alexander Abt, Winterthur (CH); Reto Grueebler, Greifensee (CH); Timo Jung, Winterthur (CH); Thomas Linsi, Schaffhausen (CH); Niccolo Maschio, Winterthur (CH)

(73) Assignee: Alcon Inc., Fribourg (CH)

( * ) Notice: Subject to any disclaimer, the term of this patent is extended or adjusted under 35 U.S.C. 154(b) by 241 days.

(21) Appl. No.: 17/000,499

(22) Filed: Aug. 24, 2020

(65) Prior Publication Data

US 2021/0059702 A1 Mar. 4, 2021

Related U.S. Application Data

(60) Provisional application No. 62/893,285, filed on Aug. 29, 2019.

(51) Int. Cl.
*A61B 17/29* (2006.01)
*A61B 17/00* (2006.01)
(Continued)

(52) U.S. Cl.
CPC .......... *A61B 17/29* (2013.01); *A61B 17/3201* (2013.01); *A61B 2017/00862* (2013.01);
(Continued)

(58) Field of Classification Search
CPC .... A61F 9/007; A61F 9/00736; A61F 2/1664; A61B 2017/305; A61B 17/2909; A61B 17/30; A61B 2017/2918
See application file for complete search history.

(56) References Cited

U.S. PATENT DOCUMENTS

D434,149 S 11/2000 Mirhashemi et al.
6,482,198 B1 11/2002 Overaker
(Continued)

FOREIGN PATENT DOCUMENTS

EP 3266393 A1 1/2018
JP 5568016 B2 8/2014
(Continued)

OTHER PUBLICATIONS

Aktive Catalog 2016, pp. 8-9 with covers (4 pages).
(Continued)

*Primary Examiner* — Elizabeth Houston
*Assistant Examiner* — Serenity A Miller

(57) ABSTRACT

Particular embodiments disclosed herein provide a surgical instrument comprising a device having a proximal end and a functional end configured to be inserted into a body part, an assembly having a proximal end and a distal end, a shaft coupled to the proximal end of the assembly, the shaft having a shaft housing, a bearing positioned around the assembly, wherein the bearing is configured to slide over the assembly, a hub having a sleeve tube. The basket comprises a plurality of grooved levers, each grooved lever having a proximal end received by the shaft housing and a distal end coupled to a tip of the basket, wherein compressing one or more of the plurality of grooved levers moves the bearing and the hub relative to the shaft and toward the functional end of the device, causing the sleeve tube to transition the device from the deactivated state to an activated state.

8 Claims, 7 Drawing Sheets

(51) Int. Cl.
  *A61B 17/3201* (2006.01)
  *A61F 9/007* (2006.01)
(52) U.S. Cl.
  CPC .............. *A61B 2017/00867* (2013.01); *A61B 2017/00955* (2013.01); *A61B 2017/2932* (2013.01); *A61F 9/007* (2013.01)

(56) References Cited

U.S. PATENT DOCUMENTS

| | | |
|---|---|---|
| 6,488,695 B1 | 12/2002 | Hickingbotham |
| 8,012,146 B2 | 9/2011 | Hickingbotham |
| 8,187,293 B2 | 5/2012 | Kirchhevel |
| 9,149,389 B2 | 10/2015 | Scheller |
| 9,173,772 B1 | 11/2015 | Scheller |
| 9,226,762 B2 | 1/2016 | Scheller |
| 9,247,951 B1 | 2/2016 | Scheller |
| 9,428,254 B1 | 8/2016 | Scheller |
| 9,480,598 B2 | 11/2016 | Clauson |
| 9,782,189 B2 | 10/2017 | Scheller |
| 9,795,506 B2 | 10/2017 | Scheller |
| D819,207 S | 5/2018 | Blank |
| 10,864,001 B2 | 12/2020 | Vezzu |
| 2002/0161398 A1 | 10/2002 | Hickingbotham |
| 2003/0171762 A1 | 9/2003 | Forchette |
| 2008/0188877 A1* | 8/2008 | Hickingbotham ......................... A61B 17/3211 606/162 |
| 2011/0214539 A1 | 9/2011 | Grand |
| 2012/0116361 A1* | 5/2012 | Hanlon ................ A61F 9/007 606/1 |
| 2012/0191120 A1 | 7/2012 | Linsi |
| 2014/0128909 A1 | 5/2014 | Scheller |
| 2014/0172010 A1 | 6/2014 | Vezzu |
| 2015/0038950 A1 | 2/2015 | Scheller |
| 2015/0173944 A1 | 6/2015 | Linsi |
| 2017/0079675 A1 | 3/2017 | Scheller |
| 2017/0086871 A1 | 3/2017 | Scheller |
| 2017/0156748 A1 | 6/2017 | Scheller |
| 2017/0340380 A1 | 11/2017 | Scheller et al. |
| 2017/0361034 A1 | 12/2017 | Scheller |
| 2018/0000643 A1 | 1/2018 | Scheller |
| 2018/0014849 A1 | 1/2018 | Scheller |
| 2018/0193192 A1 | 7/2018 | Charles |
| 2018/0235594 A1 | 8/2018 | Scheller |
| 2019/0038336 A1 | 2/2019 | Ellman et al. |
| 2019/0247229 A1 | 8/2019 | Abt |
| 2020/0187970 A1 | 6/2020 | Abt et al. |
| 2020/0246034 A1 | 8/2020 | Linsi |
| 2021/0059702 A1 | 3/2021 | Abt et al. |

FOREIGN PATENT DOCUMENTS

| | | |
|---|---|---|
| WO | 0230302 A1 | 4/2002 |
| WO | 2017066026 A1 | 4/2017 |
| WO | 2017218161 A1 | 12/2017 |
| WO | 2018017296 A1 | 1/2018 |
| WO | 2018156341 A1 | 8/2018 |
| WO | 2020157617 A1 | 8/2020 |

OTHER PUBLICATIONS

Alcon Global Vitreoretinal Product Catalog, dated Feb. 2014, pp. 1 and 25-48.
Alcon Vitreoretinal Product Catalog, Section "Hand-Held Instrumentation", copyright 2008; Nov. 2009 Update, pp. 39-52.
https://web.archive.org/web/20181217182456/http://www.katalystsurgical.com/—Ophthalmic Instruments & Eye Instruments from KatalystSurgical.com, web archive dated Dec. 17, 2018 (2 pages).
Oertli Catalog 2018, pp. 41-47 with covers (9 pages).
Katalyst Surgical, Retina Catalog, first available Feb. 2017. (https://www.labtician.com/wp-content/uploads/2019/09/KAT-01 1-REV-F-Retina-Catalog-Feb-201 7.pdf) (Year: 2017).
Leica Microsystems, Precision That Saves Eyesight, first available Apr. 28, 2010. (https://www.leica-microsystems.com/science-lab/precision-that-saves-eyesight/) (Year: 2010).
Retina Today, The Surgical Issue: All Things Retina Surgery, first available Sep. 2020. (https://retinatoday.com/pdfs/1 020us.pdf)Year: 2020).
Retinal Physician, Know Your Retinal Surgery Toolbox Options abound for today's vitrectomy operating room., first available May 1, 2018. (https://www.retinalphysician .com/issues/20 1 8/may-201 8/know-your-retinal-surgery-toolbox) (Year: 2018).

* cited by examiner

ACTUATION MECHANISM WITH GROOVED ACTUATION LEVERS

PRIORITY CLAIM

This application claims the benefit of priority of U.S. Provisional Patent Application Ser. No. 62/893,285 titled "ACTUATION MECHANISM WITH GROOVED ACTUATION LEVERS," filed on Aug. 29, 2019, whose inventors are Niels Alexander Abt, Reto Grueebler, Timo Jung, Thomas Linsi and Niccolo Maschio, which is hereby incorporated by reference in its entirety as though fully and completely set forth herein.

TECHNICAL FIELD

The present disclosure relates generally to a surgical instrument with an actuation mechanism including grooved actuation levers.

BACKGROUND

During certain surgical procedures (e.g., ophthalmic procedures) a surgeon is required to manipulate (e.g., remove, cut, peel, etc.) certain tissues within a body part by using forceps, scissors, etc. Examples of such surgical procedures are internal limiting membrane (ILM) removal and epiretinal membrane (ERM) removal for treating different macular surface diseases. During such procedures, a surgeon inserts the tip of a surgical instrument, which, for example, functions as forceps, into a patient's eye globe and uses the forceps to grasp and peel the ILM/ERM. Certain designs are currently used for providing a surgical instrument with an actuation mechanism that allows a surgeon to close and open the jaws of the forceps or scissors, which are located at the tip of a surgical instrument. However, in certain cases, the existing actuation mechanisms may, among other things, require too much actuation force and be difficult to assemble.

BRIEF SUMMARY

The present disclosure relates generally to a surgical instrument with an actuation mechanism including grooved actuation levers.

Particular embodiments disclosed herein provide a surgical instrument comprising a device having a proximal end and a functional end configured to be inserted into a body part, an assembly having a proximal end and a distal end, wherein the distal end of the assembly is coupled to the proximal end of the device, a shaft coupled to the proximal end of the assembly, the shaft having a shaft housing, a bearing positioned around the assembly, wherein the bearing is configured to slide over the assembly, a hub having a sleeve tube, wherein the sleeve tube is configured to partially house the device such that the functional end of the device at least partially extends beyond a distal end of the sleeve tube when the device is in a deactivated state, and a basket coupled to the hub. The basket comprises a plurality of levers, each grooved lever having a proximal end received by the shaft housing and a distal end coupled to a tip of the basket, wherein compressing one or more of the plurality of grooved levers moves the bearing and the hub relative to the shaft and toward the functional end of the device, causing the sleeve tube to transition the device from the deactivated state to an activated state.

The following description and the related drawings set forth in detail certain illustrative features of one or more embodiments.

BRIEF DESCRIPTION OF THE DRAWINGS

The appended figures depict certain aspects of the one or more embodiments and are therefore not to be considered limiting of the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Particular embodiments of the present disclosure provide a surgical instrument with an actuation mechanism including grooved actuation levers.

Figure 1:
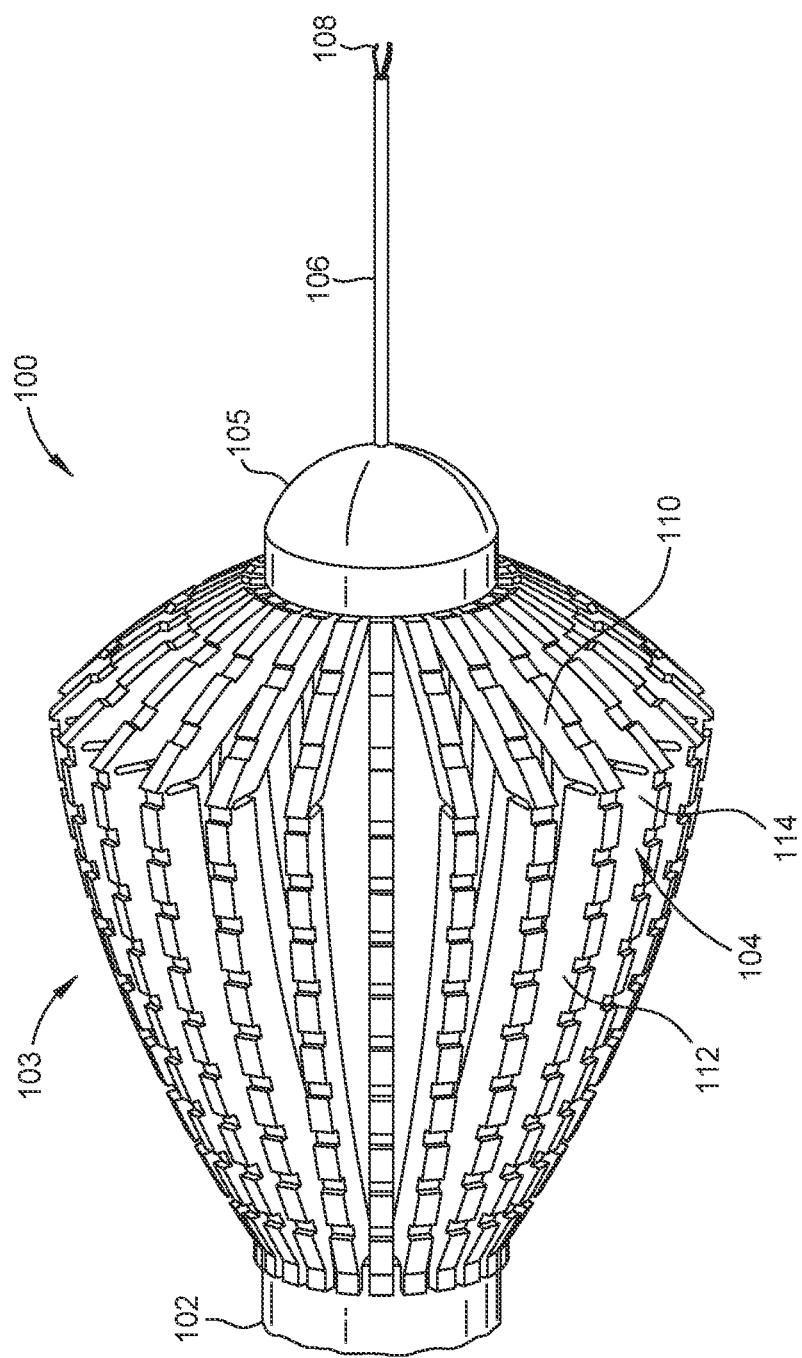
FIG. 1 illustrates an example of a surgical instrument with a prior art actuation mechanism.

FIG. 1 illustrates an example of a surgical instrument with a prior art actuation mechanism. As shown, surgical instrument 100 comprises a handle 102, a basket 103 comprising a plurality of actuation levers 104, a housing 105, an actuation tube 106, and a device, shown as forceps 108, at the tip of the probe. Each actuation lever 104 comprising a first leg 112 and a second leg 110 joined at flexible juncture 114. In other embodiments, the first leg 112 and second leg 110 may be separate pieces coupled together with a hinge. Each actuation lever 104 may be made from material such as shape memory material, titanium, stainless steel, suitable thermoplastic, etc. Actuation tube 106 may be any suitable medical grade tubing, such as titanium, stainless steel, or suitable polymer and is sized so that forceps 108 reciprocate easily within. Forceps 108 are generally made from stainless steel or titanium, but other materials may also be used.

Surgical instrument 100 is designed so that in use, when the plurality of actuation levers 104 are in their relaxed state, forceps 108 protrude or extend beyond the distal end of actuation tube 106, which is coupled to a housing 105. Squeezing one or more of the actuation levers 104 causes the respective actuation lever 104 to flex at juncture 114, pushing housing 105 forward relative to handle 102. The forward movement of housing 105 is transferred to actuation tube 106, causing actuation tube 106 to slide forward over a distal portion of the jaws of forceps 108, thereby activating forceps 108 by compressing together the jaws. By closing jaws of forceps 108, the surgeon is able to, for example, grasp and peel a tissue (e.g., ILM) within a body part.

In the example of FIG. 1, the actuation mechanism may, among other things, require too much actuation force and be too difficult to assemble. In addition, basket 103 is long and has a large diameter, which may make basket 103 too bulky. Accordingly, certain embodiments described herein relate to a surgical instrument with an actuation mechanism including grooved actuation levers. In particular embodiments, this may reduce the structural complexity of the actuation mechanism and allow for easier assembly.

Figure 2:
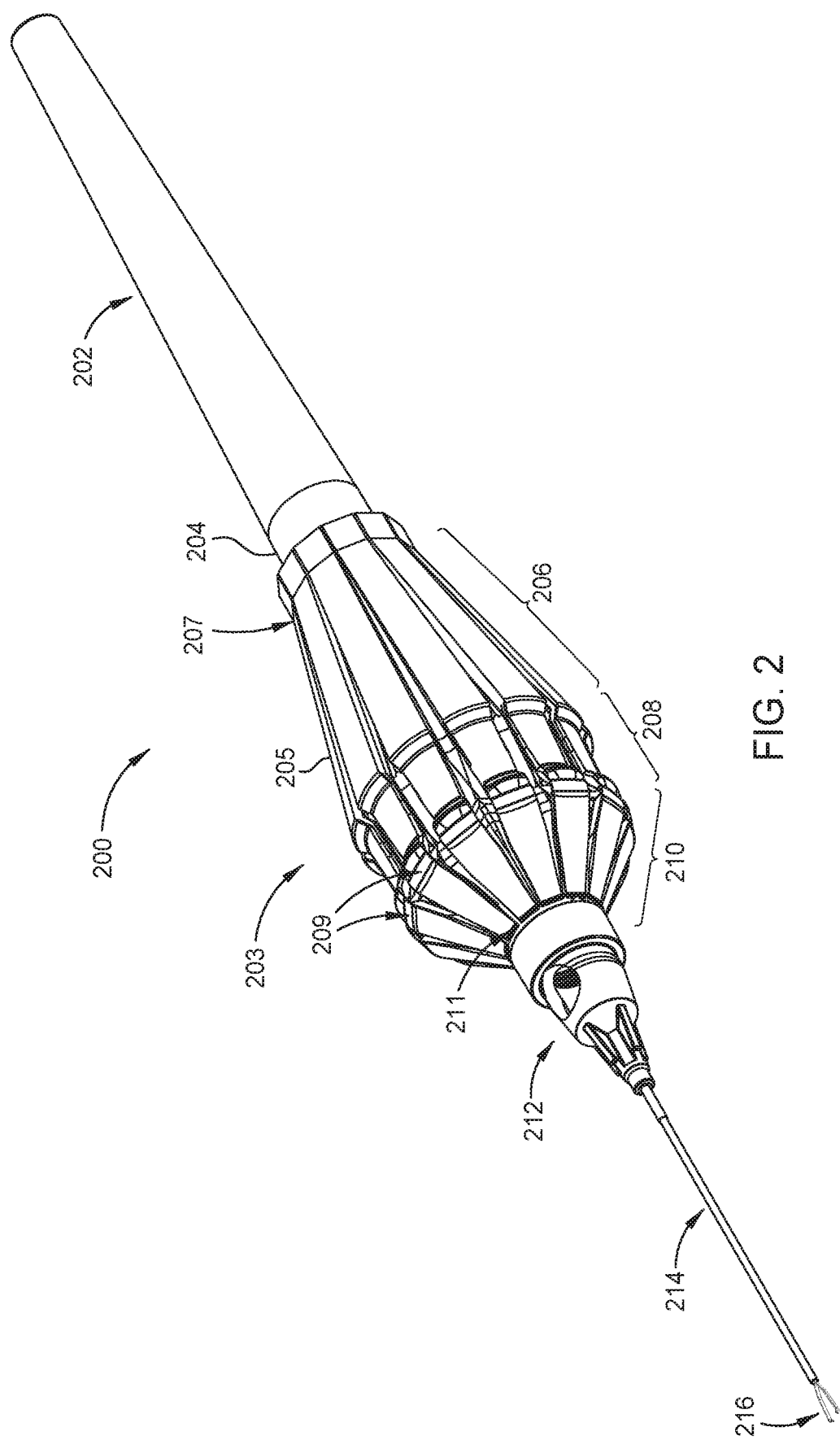
FIG. 2 illustrates a perspective view of an example surgical instrument, in accordance with certain embodiments of the present disclosure.

FIG. 2 illustrates a perspective view of an example surgical instrument 200 in accordance with the teachings of the present disclosure. As shown in FIG. 2, surgical instrument 200 comprises a rear cap 202, a shaft housing 204, a basket 203 comprising actuation levers ("levers") 205, an adjustable hub ("hub") 212 coupled to a sleeve tube 214, and device 216.

Although in the example of FIG. 2, device 216 is shown as forceps, generally device 216 may be any surgical device that is shaped to fit in sleeve tube 214 with a distal end that is referred to as a functional end (e.g., a movable or active end). For example, device 216 may be shaped as a needle with a functional end, which may comprise forceps, scissors, etc., with jaws or arms. The proximal end of device 216 is coupled to a coupling tube of a snapper assembly, as shown in FIGS. 3, 4, 5A-5B, etc.

As used herein, the term "proximal" refers to a location with respect to a device or portion of the device that, during normal use, is closest to the clinician using the device and farthest from the patient in connection with whom the device is used. Conversely, the term "distal" refers to a location with respect to the device or portion of the device that, during normal use, is farthest from the clinician using the device and closest to the patient in connection with whom the device is used.

Basket 203 couples to shaft housing 204 at its proximal end and to hub 212 at its distal end. Shaft housing 204 is part of a shaft that extends longitudinally within basket 203. At its proximal end, the shaft couples to rear cap 202. Basket 203 comprises levers 205, each lever 205 including a first leg 206 and a second leg 210, the second leg 210 comprising a grooved segment 208. In certain aspects, the length of first leg 206 may be in the range of 18-30 millimeters (mms), the length of grooved segment 208 may be in the range of 4-8 mms, and the length of the second leg 210 may be in the range of 9-18 mms. Grooved segments 208 of levers 205 allow a user, such as a surgeon, to more easily grasp and actuate surgical instrument 200 as compared to the prior art basket design shown in FIG. 1. The outer diameter of basket 203, where the grooved segments 208 are, is smaller than the outer diameter of basket 203 where the distal ends of first legs 206 or the proximal ends of the un-grooved segments of the second legs 210 are. For example, the outer diameter of basket 203, where the grooved segments 208 are, is 0.1 to 0.8 millimeters (mms) smaller than the outer diameter of basket 203 where the distal ends of first legs 206 or the proximal ends of the un-grooved segments of the second legs 210 are.

Each lever 205 also comprises three moving joints or junctures 207, 209, and 211, which allow the lever to extend when it is compressed. More specifically, each lever 205 comprises a tail joint 207, a main joint 209, and a head joint 211, which allow the lever to bend and extend. These joints allow basket 203 to be compressed thereby pushing hub 212 along with sleeve tube 214 forward relative to shaft housing 204. In certain embodiments, each of tail joint 207, main joint 209, and head joint 211 may comprise a hinge.

Although not shown, the inner surface of hub 212 and the outer surface of the distal end of basket 203 may be threaded, thereby allowing hub 212 to be screwed on to the distal end of basket 203. Hub 212 is adjustable meaning that, during the manufacturing process, screwing hub 212 clockwise or counterclockwise allows for adjusting how far the functional end of device 216 extends beyond the distal end of sleeve tube 214. For example, a larger portion of the functional end of device 216 protrudes beyond sleeve tube 214 when hub 212 is fully rotated or screwed on to the distal end of basket 203. By screwing hub 212 counterclockwise, however, hub 212 and sleeve tube 214 move in a distal direction relative to basket 203, which causes the distal end of sleeve tube 214 to cover a larger portion of the functional end of device 216, as compared to when hub 212 is fully screwed on to the distal end of basket 203.

Figure 6A:
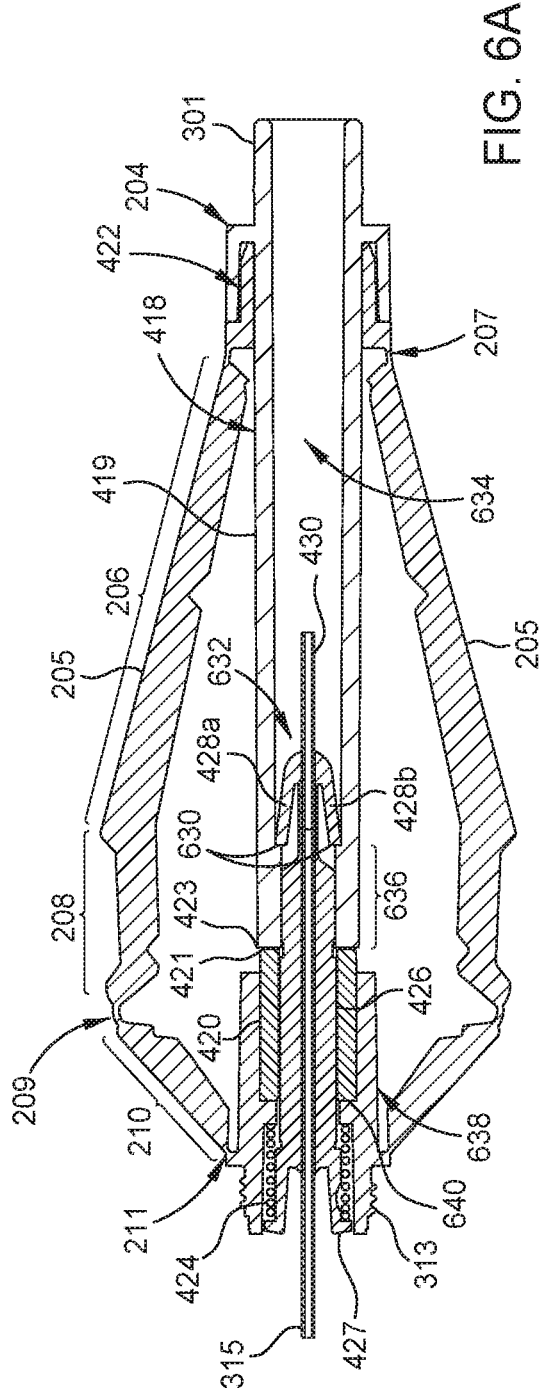
FIG. 6A illustrates a cross sectional view of the surgical instrument of FIG. 2, when levers of the surgical instrument are in their at-rest state, in accordance with certain embodiments of the present disclosure.
Figure 6B:
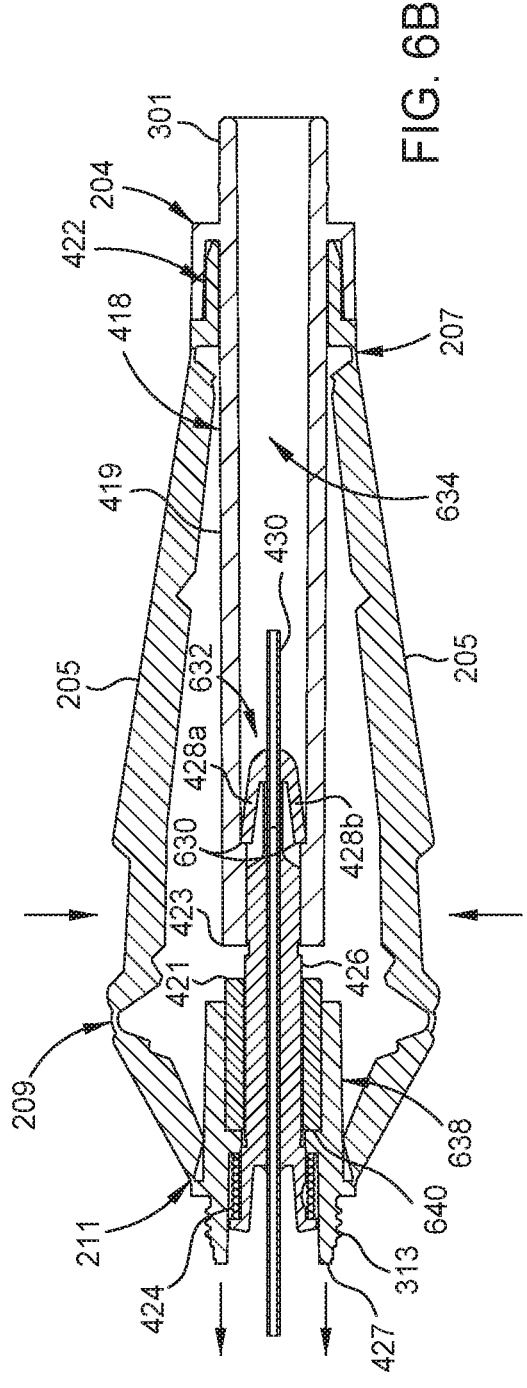
FIG. 6B illustrates a cross sectional view of the surgical instrument of FIG. 2, when levers of the surgical instrument are in their compressed state, in accordance with certain embodiments of the present disclosure.

Surgical instrument 200 is designed so that in use, when levers 205 are in their relaxed or at-rest state (i.e., not compressed), the functional end of device 216 protrudes or extends beyond the distal end of sleeve tube 214. In other words, sleeve tube 214 only partially covers the functional end of device 216. When levers 205 are compressed, the distal end of basket 203 is pushed forward relative to shaft housing 204 and device 216. The forward movement of the distal end of basket 203 is transferred to hub 212 and then sleeve tube 214, causing sleeve tube 214 to slide forward and activate device 216. Device 216 is activated as a result of the forward movement of sleeve tube 214, which presses the jaws or arms of device 216 together. An activated device refers to a device whose jaws or arms are closed. Note that FIG. 2 illustrates levers 205 in their at-rest state while FIG. 6B illustrates a cross sectional view of surgical instrument 200 when levers 205 are compressed.

Levers 205 are made from flexible but resilient material to allow levers 205 to be compressed and then pushed back into their at-rest positions. In one example, levers 205 may be made from polyoxymethylene (POM). Note that in the example of FIG. 2, surgical instrument 200 comprises 12 levers 205. However, a fewer or larger number of levers 205 may be used in other embodiments. For example, surgical instrument 200 may have between 10-16 levers.

Figure 3:
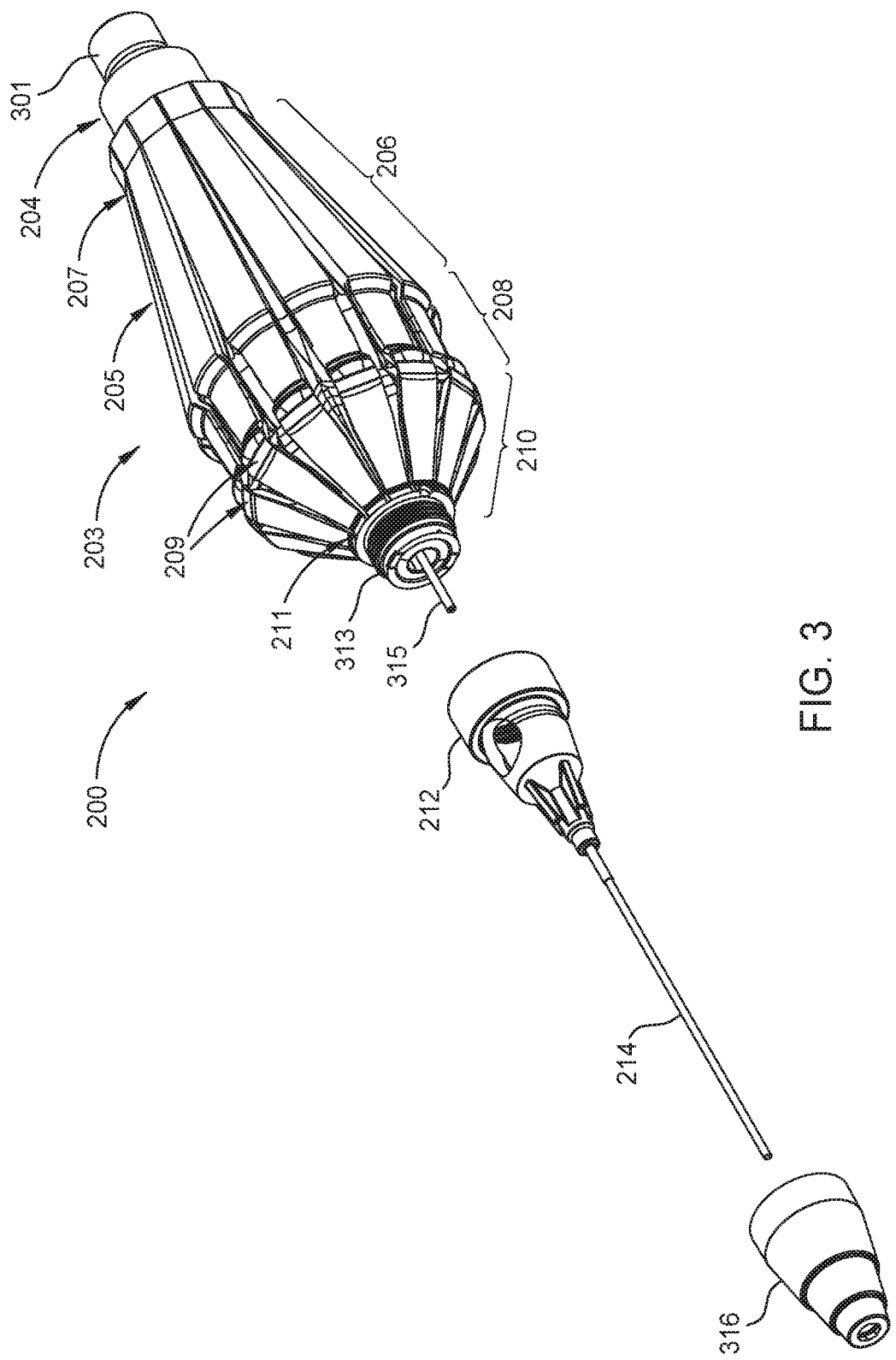
FIG. 3 illustrates a perspective view of a hub and a basket of the surgical instrument of FIG. 2, in accordance with certain embodiments of the present disclosure.

FIG. 3 illustrates a perspective view of hub 212 and basket 203 of surgical instrument 200 separately. As shown, hub 212 can be screwed on to a threaded tip or segment 313 of basket 203. FIG. 3 also shows a coupling tube 315 of a snapper assembly that is positioned inside of basket 203. Coupling tube 315 protrudes outside or beyond threaded segment 313. The distal end of coupling tube 315 is configured to be coupled to a proximal end of a needle of device 216. In some embodiments, the distal end of coupling tube 315 and the proximal end of the needle of device 216 are crimped together. FIG. 3 also shows a cap 316 that is configured to house hub 212. Cap 316 is placed on hub 212 upon the completion of the manufacturing process, which includes the adjustment of hub 212. FIG. 3 also shows the proximal end 301 of the shaft, described in further detail below. Proximal end 301 of the shaft is configured to be coupled to rear cap 202.

Figure 4:
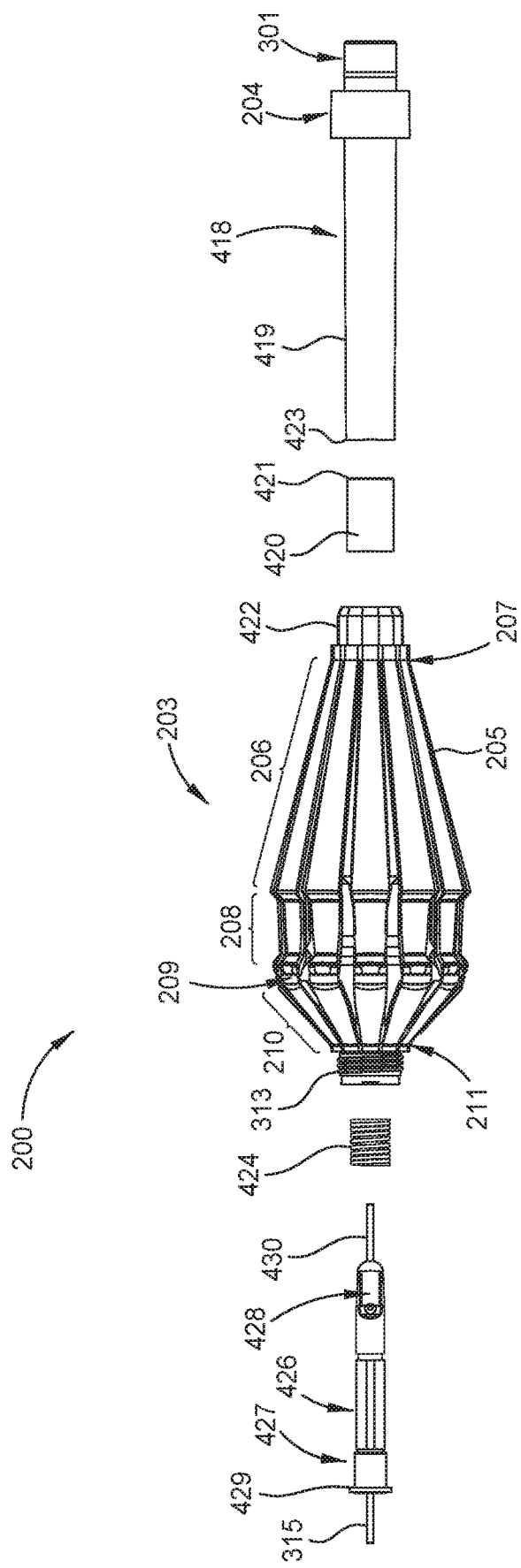
FIG. 4 illustrates an exploded view of some of the components of the surgical instrument of FIG. 2, in accordance with certain embodiments of the present disclosure.

FIG. 4 illustrates an exploded view of some of the components of surgical instrument 200. As shown, basket 203 comprises an insert 422 at its proximal end, which is configured to be inserted into a cylindrical opening between the body of shaft 418 and shaft housing 204. More specifically, insert 422, in some embodiments, may be friction-locked into the opening. Shaft 418 comprises an extended cylindrical portion 419 that is configured to longitudinally extend within basket 203. Shaft 418 comprises a hollow compartment to allow the proximal end of snapper assembly 426 to be inserted (or received) and snapped therein, as further described in relation to FIGS. 6A-6B.

Also shown is a bearing 420, which is configured to be positioned at the distal end of cylindrical portion 419 of shaft 418. As shown in FIGS. 6A and 6B, bearing 420 is also configured to slide on snapper assembly 426 after snapper assembly 426 is snapped into the hollow compartment of shaft 418. Bearing 420 is also configured to be housed by a bearing housing of basket 203, as shown in FIGS. 6A and 6B in more detail. When levers 205 are in their at-rest state, the proximal end 421 of bearing 420 and the distal end 423 of shaft 418 are in contact. However, when levers 205 are in their compressed state, bearing 420 slides forward relative to shaft 418 and snapper assembly 426 such that the proximal end 421 of bearing 420 and the distal end 423 of shaft 418 are no longer in contact. Bearing 420's inner surface is made of or comprises material that has a low friction coefficient with respect to the outer surface of the snapper assembly 426. As a result, utilizing bearing 420 in the actuation mechanism described herein is advantageous because it allows for a smoother actuation, as bearing 420 is able to smoothly slide back and forth on snapper assembly 426.

Figure 5A:
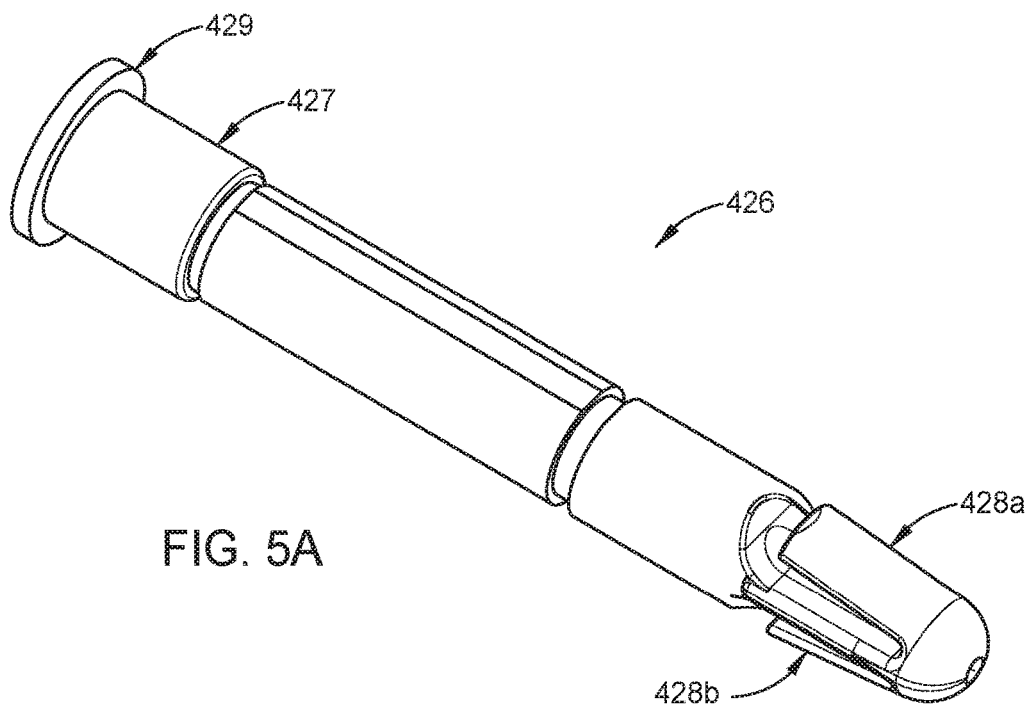
FIGS. 5A-5C illustrate different views of a snapper assembly of the surgical instrument of FIG. 2, in accordance with certain embodiments of the present disclosure.
Figure 5B:
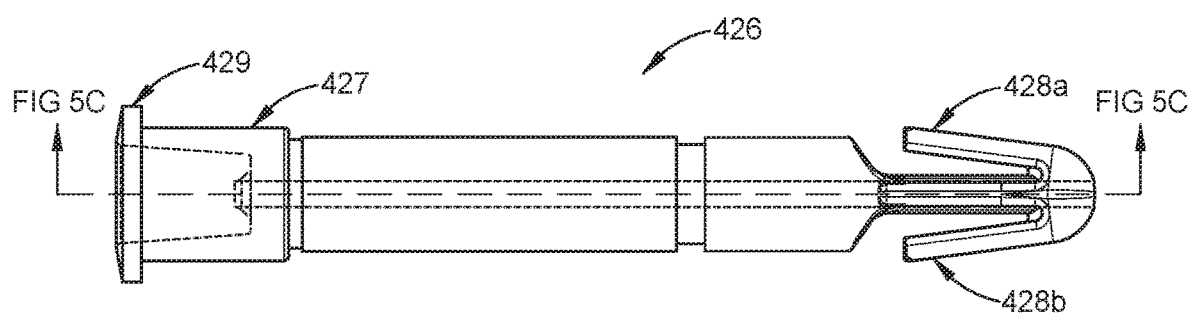
Figure 5C:
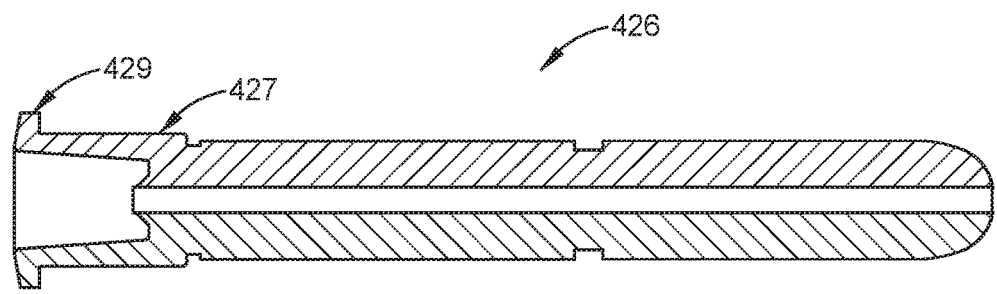

Snapper assembly 426 comprises a needle-shaped proximal end 430, which, as described above, is configured to be inserted into the hollow compartment of shaft 418. Snapper assembly 426 also comprises wings 428, which are biased outwardly and configured to snap into the hollow compartment of shaft 418. Once wings 428 snap into the hollow compartment, snapper assembly 426 does not move relative to shaft 418. Different views of snapper assembly 426 are shown in FIGS. 5A-5C, which illustrate wings 428 more clearly. Snapper assembly 426 also comprises a cylindrical element 427 around which spring 424 is configured to be positioned. The distal end of spring 424 is positioned against barrier 429 of snapper assembly 426. When basket 203 is compressed, the distal end of threaded segment 313 moves in a distal direction relative to shaft 418 and compresses spring 424 against barrier 429. As a result, spring 424 becomes loaded or charged, thereby causing basket 203 to transition or snap back into its at-rest position when the user releases basket 203.

Utilizing the basket design of basket 203 in the actuation mechanism described herein is advantageous because less actuation force is required to compress basket 203 and thereby activate the device (e.g., device 216) used in conjunction with or as part of surgical instrument 200. More specifically, the diameter of basket 203 (e.g., in the range of 11-23 mms) is smaller at or over the grooved segment 208 of basket 203 as compared to the diameter of basket 103, of the prior art actuation mechanism, at junctures 114. As a result, with the actuation mechanism described herein a lower amount of force is applied to spring 424 and, therefore, a lower amount of opposite spring force is experienced by the user when compressing basket 203. Also, as described above, grooved segments 208 of levers 205 allow for a user to more easily grasp and compress basket 203. In certain aspects, spring 424's spring constant is in the range of 0.2-1 Newton/millimeter (N/mm).

FIGS. 5A-5C illustrate different views of snapper assembly 426. FIG. 5A illustrates a perspective view of snapper assembly 426, which comprises wings 428a and 428b, barrier 429 and cylindrical element 427. FIG. 5B illustrates a side view of snapper assembly 426. FIG. 5C illustrates a cross sectional view of snapper assembly 426.

FIG. 6A illustrates a cross sectional view of surgical instrument 200 when levers 205 are in their at-rest state. As shown, insert 422 is positioned within the cylindrical opening between the body of shaft 418 and shaft housing 204. Also shown is snapper assembly 426, which is snapped into a hollow compartment 632 of shaft 418. As described above, wings 428a-428b are biased outwardly such that to insert snapper assembly 426 into hollow compartment 632, wings 428a-428b would have to be pushed inwardly towards a longitudinal axis of snapper assembly 426.

During the assembly process of surgical instrument 200, needle-shaped proximal end 430 may be used as a guide to insert snapper assembly 426 into hollow compartment 632. At a certain point, by pushing snapper assembly 426 far enough, wings 428a-428b snap into hollow compartment 632. More specifically, once snapper assembly 426 is fully inserted into hollow compartment 632, the tips of wings 428a-428b snap into the distal end of hollow compartment 632, at which point the inner diameter of shaft 418 is larger. What allows the tips of wings 428a-428b to snap into the distal end of hollow compartment 632 is the difference in the inner diameter of shaft 418 at its different portions. For example, as shown, shaft 418 has a smaller inner diameter at portion 636 in comparison with the inner diameter of shaft 418 at the distal end of hollow compartment 632. Once wings 428a-428b snap into hollow compartment 632, snapper assembly 426 is locked in place and can no longer be separated from shaft 418 because the proximal end of portion 636 acts as a barrier against the tips of wings 428-428b.

As shown, the distal end 423 of shaft 418 is in contact with the proximal end 421 of bearing 420 when levers 205 are in their at-rest state. Bearing 420 is positioned in an opening between bearing housing 638 and snapper assembly 426. More specifically, the opening is provided between the inner surface of bearing housing 638, which is cylindrically shaped, and the outer surface of snapper assembly 426. As shown, the distal end of bearing 420 is in contact with the end of the opening, which refers to the proximal end of a slider segment 640 of bearing housing 638. Slider segment 640 does not make contact with the body of snapper assembly 426 and moves relative to shaft 418 when levers 205 are compressed. Slider segment 640 is positioned at the distal end of bearing housing 638. As described above, FIG. 6A illustrates levers 205 in their at-rest state, meaning that the device (e.g., device 216) is in an inactivated state (e.g., the jaws of the forceps are open).

FIG. 6B illustrates a cross sectional view of surgical instrument 200 when levers 205 are in their compressed state. As shown, when levers 205 are compressed, the distal end of levers 205 move in a distal direction, meaning slider segment 640 moves in a distal direction, thereby pressing spring 424 against barrier 429, which results in spring 424 exerting opposite spring force against slider segment 640. As shown, bearing 420 has moved in a distal direction relative to shaft 418, such that there is now some space between the proximal end 421 of bearing 420 and the distal end 423 of shaft 418. As described above, because the inner surface of bearing 420 has a low friction coefficient with the outer surface of snapper assembly 426, bearing 420 is able to smoothly slide over snapper assembly 426, thereby resulting in a smooth actuation. When levers 205 are compressed, the hub and the sleeve tube (e.g., hub 212 and sleeve tube 214) move toward the functional end of the device, causing the sleeve tube to transition the device from a deactivated state to an activated state (e.g., forceps jaws are closed). Note that, in the example of FIGS. 6A-6B, basket 203 is manufactured as a single component (e.g., through injection molding), although in some other embodiments, that need not be the case.

Figure 7A:
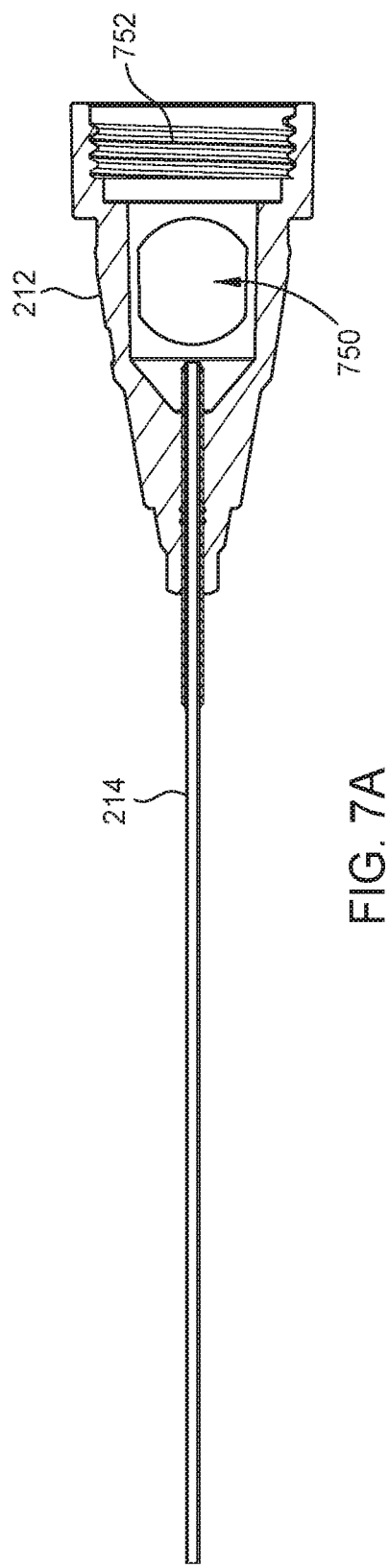
FIGS. 7A-7B illustrate different views of the hub of the surgical instrument of FIG. 2, in accordance with certain embodiments of the present disclosure.
Figure 7B:
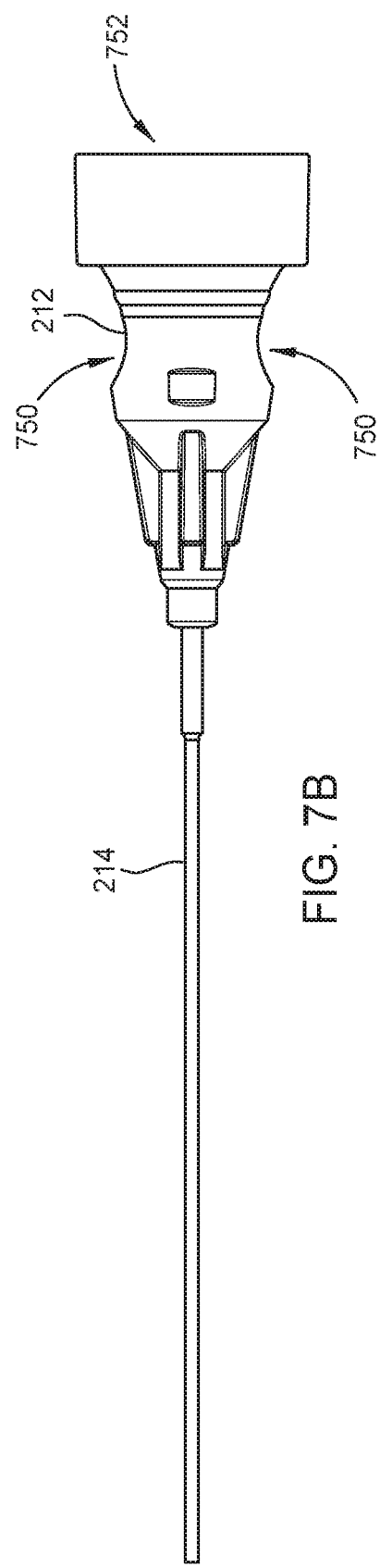

FIGS. 7A-7B illustrate different views of a hub 212. FIG. 7A illustrates a cross-sectional view of hub 212. As shown, hub 212 comprises a threaded opening 752, which allows hub 212 to be screwed on to the threaded segment 313 of basket 203. Hub 212 also comprises an opening 750 through which the position of the device can be adjusted. For example, during the assembly process of the surgical device, after hub 212 is coupled to basket 203, the proximal end of device 216 may be inserted into the sleeve tube 214 in order to couple the proximal end of device 216 to coupling tube 315 of snapper assembly 426. During this process, the proximal end of device 216 passes through opening 750 and is, therefore, accessible through the opening. As a result, the position of the device 216 may be adjusted using an instrument that is able to grab on to device 216 through opening 750. For example, device 216 may be further pushed in to ensure that its proximal end is fully coupled to coupling tube 315 using such an instrument through opening 750.

FIG. 7B illustrates a side view of hub 212 with a 90-degree rotation about an axis parallel to sleeve tube 214. As shown, hub 212 comprises two openings 750, shown from the side.

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

What is claimed is:

1. A surgical instrument, comprising:
a device having a proximal end and a functional end configured to be inserted into a body part;
an assembly having a proximal end and a distal end, wherein the distal end of the assembly is coupled to the proximal end of the device;
a shaft coupled to the proximal end of the assembly, the shaft having a shaft housing;
a bearing positioned around the assembly, wherein the bearing is configured to slide over the assembly;
a hub having a sleeve tube, wherein the sleeve tube is configured to partially house the device such that the functional end of the device at least partially extends beyond a distal end of the sleeve tube when the device is in a deactivated state; and
a basket coupled to the hub, the basket comprising:
a plurality of grooved levers, each grooved lever having a proximal end received by the shaft housing and a distal end coupled to a tip of the basket, wherein compressing one or more of the plurality of grooved levers moves the bearing and the hub relative to the shaft and toward the functional end of the device, causing the sleeve tube to transition the device from the deactivated state to an activated state;

wherein:
the basket comprises a bearing housing; and
the bearing is positioned in an opening provided between the bearing housing and a body of the assembly;
wherein:
a proximal end of the bearing is in contact with a distal end of the shaft when the plurality of levers are in an at-rest state;
the device is de-activated when the plurality of levers are in the at-rest state; and
the proximal end of the bearing is separated from the distal end of the shaft when the plurality of levers are compressed.

2. The surgical instrument of claim 1, wherein:
each of the plurality of grooved levers comprises a first leg and a second leg, the second leg comprising a grooved segment; and
a first outer diameter of the basket over grooved segments of the plurality of grooved levers is smaller than a second outer diameter of the basket at distal ends of first legs of the plurality of grooved levers and proximal ends of un-grooved segments of second legs of the plurality of grooved levers.

3. A surgical instrument, comprising:
a device having a proximal end and a functional end configured to be inserted into a body part;
an assembly having a proximal end and a distal end, wherein the distal end of the assembly is coupled to the proximal end of the device;
a shaft coupled to the proximal end of the assembly, the shaft having a shaft housing;
a bearing positioned around the assembly, wherein the bearing is configured to slide over the assembly;
a hub having a sleeve tube, wherein the sleeve tube is configured to partially house the device such that the functional end of the device at least partially extends beyond a distal end of the sleeve tube when the device is in a deactivated state; and
a basket coupled to the hub, the basket comprising:
a plurality of grooved levers, each grooved lever having a proximal end received by the shaft housing and a distal end coupled to a tip of the basket, wherein compressing one or more of the plurality of grooved levers moves the bearing and the hub relative to the shaft and toward the functional end of the device, causing the sleeve tube to transition the device from the deactivated state to an activated state;
wherein:
the assembly comprises a snapper assembly having one or more wings; and
the shaft comprises a hollow compartment configured to receive the proximal end of the snapper assembly and the one or more wings of the snapper assembly.

4. The surgical instrument of claim 3, wherein the one or more wings are snapped and locked into the hollow compartment.

5. The surgical instrument of claim 4, wherein:
each of the plurality of grooved levers comprises a first leg and a second leg, the second leg comprising a grooved segment; and
a first outer diameter of the basket over grooved segments of the plurality of grooved levers is smaller than a second outer diameter of the basket at distal ends of first legs of the plurality of grooved levers and proximal ends of un-grooved segments of second legs of the plurality of grooved levers.

6. The surgical instrument of claim 3 wherein:
each of the plurality of grooved levers comprises a first leg and a second leg, the second leg comprising a grooved segment; and
a first outer diameter of the basket over grooved segments of the plurality of grooved levers is smaller than a second outer diameter of the basket at distal ends of first legs of the plurality of grooved levers and proximal ends of un-grooved segments of second legs of the plurality of grooved levers.

7. A surgical instrument, comprising:
a device having a proximal end and a functional end configured to be inserted into a body part;
an assembly having a proximal end and a distal end, wherein the distal end of the assembly is coupled to the proximal end of the device;
a shaft coupled to the proximal end of the assembly, the shaft having a shaft housing;
a bearing positioned around the assembly, wherein the bearing is configured to slide over the assembly;
a hub having a sleeve tube, wherein the sleeve tube is configured to partially house the device such that the functional end of the device at least partially extends beyond a distal end of the sleeve tube when the device is in a deactivated state; and
a basket coupled to the hub, the basket comprising:
a plurality of grooved levers, each grooved lever having a proximal end received by the shaft housing and a distal end coupled to a tip of the basket, wherein compressing one or more of the plurality of grooved levers moves the bearing and the hub relative to the shaft and toward the functional end of the device, causing the sleeve tube to transition the device from the deactivated state to an activated state;
wherein:
the hub comprises a threaded opening;
the tip of the basket comprises a threaded segment, wherein the threaded opening is configured to be screwed onto the threaded segment of the tip of the basket; and
adjusting a position of the hub with respect to the basket allows for adjusting how far the functional end of the device extends beyond the distal end of the sleeve tube.

8. The surgical instrument of claim 7, wherein the hub comprises two openings through which a position of the device within the surgical instrument can be adjusted and fixed.

* * * * *